United States Patent [19]

Muller et al.

[11] 4,065,433

[45] Dec. 27, 1977

[54] PROCESS FOR THE MANUFACTURE OF POLYADDITION PRODUCTS CONTAINING IMIDE GROUPS

[75] Inventors: Albrecht Muller, Allschwil; Theobald Haug, Frankendorf; Alfred Renner, Munchenstein, all of Switzerland

[73] Assignee: Ciba-Geigy Corporation, Ardsley, N.Y.

[21] Appl. No.: 534,104

[22] Filed: Dec. 18, 1974

[30] Foreign Application Priority Data

| Dec. 21, 1973 | Switzerland | 18051/73 |
| Dec. 21, 1973 | Switzerland | 18052/73 |
| Feb. 7, 1974 | Switzerland | 1769/74 |
| Feb. 7, 1974 | Switzerland | 1770/74 |

[51] Int. Cl.$^2$ .................... C08G 73/12; C08G 73/16
[52] U.S. Cl. .................... 260/47 UA; 260/78 UA; 260/78.41; 526/11.1
[58] Field of Search ........ 260/78.4 R, 78 UA, 47 UA; 526/11.1

[56] References Cited
U.S. PATENT DOCUMENTS

| 3,821,164 | 6/1974 | Relles | 260/47 UA |
| 3,868,351 | 2/1975 | Hand et al. | 260/78 UA |
| 3,878,172 | 4/1975 | Bargain et al. | 260/78 UA |
| 3,947,385 | 3/1976 | Schmitter et al. | 260/78 UA |
| 3,948,861 | 4/1976 | Bargain | 260/78 UA |
| 3,950,279 | 4/1976 | Haug et al. | 260/78 UA |
| 3,960,812 | 6/1976 | Renner et al. | 260/78 UA |
| 3,966,531 | 6/1976 | Bargain | 260/78 UA |
| 3,970,714 | 7/1976 | Bargain | 260/78 UA |
| 3,979,350 | 9/1976 | Winter | 260/78 UA |

*Primary Examiner*—Alan Holler
*Attorney, Agent, or Firm*—Nestor W. Shust

[57] ABSTRACT

According to the invention, polyaddition products containing imide groups are manufactured by reacting certain polyimides (preferably maleimides) with polyhydric alcohols in the presence of basic compounds. The preferred embodiment (E) relates to the use of catalysts as basic compounds. In particular, amines and alkali metal compounds can be used. A further embodiment (F) relates to the use of primary polyamines as basic compounds. In the latter case, the polyamine participates in the polyaddition mechanism, that is to say the molecules are incorporated into the polyaddition products. In this latter case, catalysts can also be used additionally.

61 Claims, No Drawings

PROCESS FOR THE MANUFACTURE OF POLYADDITION PRODUCTS CONTAINING IMIDE GROUPS

The invention can be utilised particularly in the fields of surface protection, the electrical industry, laminating processes, the manufacture of foamed plastics and the building industry.

It is known that polymaleimides can be used as raw materials for the manufacture of polyaddition products and polymerisation products. Thus, for example, French Pat. No. 1,555,564 describes the polyaddition of N,N'-bis-maleimides with primary diamines and the curing of these pre-adducts by thermal polymerisation. The resulting polymers, containing succinimide radicals, are however inadequate for many applications. This is because they have a comparatively low heat distortion point.

U.S. Pat. No. 3,741,942 claims polyaddition products obtained from bis-maleimides and organic dithiols. These known polyadducts, and their process of manufacture, all have the great disadvantages characteristic of high polymers containing sulphur. In particular, the strongly objectionable odour attributable to the dithiols, and the toxic action of the latter, should be pointed out. Since analogous objectionable characteristics also manifest themselves on combustion, and on high temperature decomposition, of these polyadducts containing sulphur, the materials can in most cases not be employed as constructional materials, especially in the building industry, in automobile construction and in aircraft construction. A further disadvantage of these products which should be mentioned is that the softening points are no higher than 110° to 170° C.

It is the object of the invention to provide polycondensation products, containing imide groups, which are based on polymaleimides, do not exhibit the disadvantages of the previously known polyadducts based on polymaleimide, and can be manufactured without handling materials which are harmful to health, and without objectionable odours.

The invention relates to a process for the manufacture of polyaddition products containing imide groups, which is characterised in that polyimides which contain, per molecule, at least two radicals of the general formula

in which D denotes a divalent radical containing a carbon-carbon double bond, are reacted with polyhydric alcohols in the presence of basic compounds at temperatures between 50° and 280° C.

According to a preferred embodiment (E) of the invention, the basic compounds employed are catalysts. The polyimides and the polyhydric alcohols are preferably employed in such amounts as to provide 0.1 to 1 equivalent of polyhydric alcohol per 1 equivalent of polyimide.

Basic catalysts present according to the invention are in particular tertiary, secondary or primary amines, or amines which contain several different types of amino groups (for example mixed tertiary-secondary amines) and quaternary ammonium compounds. These amine catalysts can be either monoamines or polyamines. Where primary and secondary amines are used, monoamines are to be preferred. The following substances may be listed as examples of such amine catalysts: diethylamine, tributylamine, triethylamine, triamylamine, benzylamine, N-methylpyrrolidine, tetramethyldiaminodiphenylmethane, quinoline, N,N-diisobutylaminoacetonitrile, N,N-dibutylaminoacetonitrile, imidazole, benzimidazole and their homologues and also mercaptobenzothiazole. Benzyltrimethylammonium hydroxide and benzyltrimethylammonium methoxide may be mentioned as examples of suitable quaternary ammonium compounds.

Further suitable catalysts are alkali metal compounds, such as alkali metal alcoholates and alkali metal hydroxides. Sodium methylate is particularly suitable.

The catalysts should be present in the reaction mixture in a concentration of 0.01 to 15% by weight, preferably of 0.05 to 10% by weight, the % by weight data being relative to the total amount of the reacting starting components.

The products produced by the reactions, which contain secondary or tertiary amino groups, can also act as catalysts during the course of the reaction.

A further preferred embodiment (F) of the present invention is the use of primary polyamines as basic compounds, the procedure followed being such as to provide, per 1 equivalent of polyimide, such an amount of polyhydric alcohol and primary polyamine that the sum of the two latter substances is 0.2 to 1.5 equivalents and the equivalent ratio of the polyhydric alcohol to the polyamine is 1 : 4 to 4 : 1. Preferably, the equivalent ratio of the polyhydric alcohol to the polyamine should be 1 : 2 to 4 : 1.

The polyaddition, according to the invention, is based entirely or partially on a novel linking of polyamide and polyhydric alcohol in accordance with the following chemical equation (I-P), in which, for simplicity, difunctional reactants and a bis-maleimide are employed.

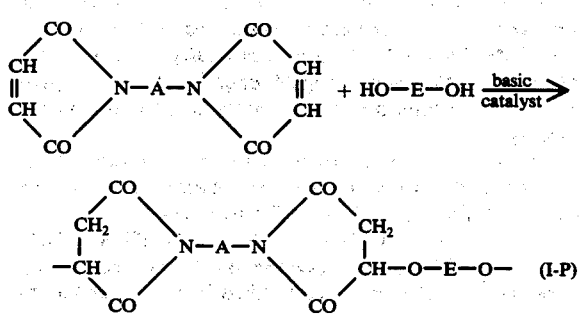

In the case of the preferred embodiment (F) of the invention, the polyaddition is further based on linking of polyimide and polyamine in accordance with the following chemical equation (I-A), in which, for simplicity, difunctional reactants and a bis-maleimide are again employed.

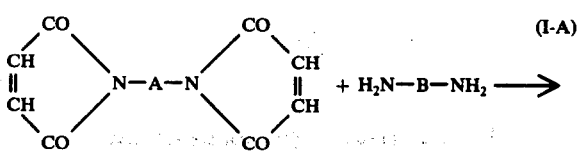

-continued

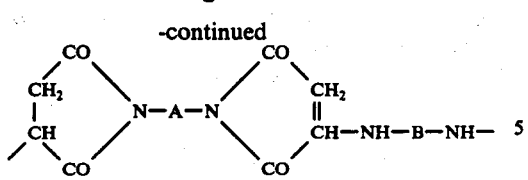

Both types of linking lead in the first instance to molecular chains, and in case (F) chain members produced according to equations (I-A) and (I-P) can be incorporated into the chains alternately, in statistical distribution, or separately, that is to say each cumulatively in the form of a block polymer.

In the course of the reaction according to the invention, a crosslinking reaction also occurs, which is principally based on the homopolymerisation of the double bonds of the polyimides employed. This crosslinking is particularly effective if the number of double bond equivalents is greater than the sum of the amino equivalents and hydroxyl equivalents. The formation of crosslinked products is particularly obvious if trifunctional or higher-functional starting products are used.

The polyaddition which takes place when carrying out the process according to the invention was particularly surprising, in the light of the relevant literature, with regard to the linking according to the scheme of the above equation (I-P).

Thus, for example, a publication by R. A. Finnegan and W. H. Mueller and J. Pharmaceutical Sciences 54 (1965) 1257-1260 describes the reaction of methanol with N-phenylmaleimide in the presence of aqueous sodium hydroxide solution at room temperature. The reaction mechanism postulated is first a splitting open of the imide ring with addition of methanol and then the addition of a second methanol molecule to the double bond.

Taking into account this state of the art, it was not to be expected at all that when applying the teaching for a technical process provided by the invention to the reactants polymaleimide and polyhydric alcohol, a polyaddition would take place, with preservation of the imide rings and formation of ether groups, according to equation (I-P). This polyaddition, optionally together with the polyaddition according to equation (I-A), surprisingly leads to high polymers which have excellent heat stability.

Most of the polyimides which can be employed according to the invention are described in detail in the literature. They can be manufactured according to the methods described in U.S. Pat. No. 3,010,290 and G.B. Pat. No. 1,137,592, by reaction of the corresponding diamines with the unsaturated dicarboxylic acid anhydrides.

According to the invention it is possible to employ, inter alia, all the polyimides which have already been listed in French Patent No. 1,555,564. Maleimides, that is to say polyimides of the formula (I), in which D denotes the divalent radical of the formula

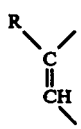 (II)

wherein R represents hydrogen or methyl, are particularly suitable.

A preferred embodiment of the invention is the reaction with polyimides which contain, per molecule, two or three radicals of the formula (I) and hence, in particular, the reaction with bis-maleimides and tris-maleimides.

Particularly suitable bis-maleimides which should be mentioned are compounds of the formula

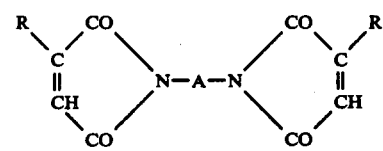 (III)

in which A denotes a divalent organic radical with 2 to 30 C atoms.

The radical A in the formula (III) preferably corresponds to the formula

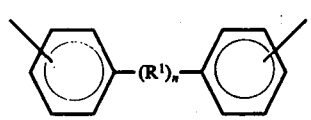 (IV)

wherein $R^1$ is one of the radicals —CH$_2$—,

—SO$_2$—, —SO—, —S— and —O— and $n$ is 0 or 1.

The following substances may be mentioned as special examples of known polyimides which are suitable for the process according to the invention: N,N'-ethylene-bis-maleimide, N,N'-hexamethylene-bis-maleimide, N,N'-m-phenylene-bis-maleimide, N,N'-p-phenylene-bis-maleimide, N,N'-4,4'-diphenylmethane-bis-maleimide, N,N'-4,4'-3,3'-dichloro-diphenylmethane-bis-maleimide, N,N'-4,4'-diphenyl-ether bis-maleimide, N,N'-4,4'-diphenylsulphone-bis-maleimide, N,N'-4,4'-dicyclohexylmethane-bis-maleimide, N,N'-α,α'-4,4'-dimethylenecyclohexane-bis-malemide, N,N'-m-xylylene-bis-maleimide, N,N'-p-xylylene-bis-maleimide, N,N'-4,4'-diphenylcyclohexane-bis-maleimide, N,N'-m-phenylene-bis-citraconimide, N,N'-4,4'-diphenylmethane-bis-citraconimide, N,N'-4,4'-2,2-diphenylpropane-bis-maleimide, N,N'-γ,γ'-1,3-dipropylene-5,5-dimethyl-hydantoin-bis-maleimide, N,N'-4,4'-diphenylmethane-bis-itaconimide, N,N'-p-phenylene-bis-itaconimide, N,N'-4,4'-diphenylmethane-bis-dimethylmaleimide, N,N'-4,4'-2,2-diphenylpropane-bis-dimethylmaleimide, N,N'-hexamethylene-bis-dimethylmaleimide, N,N'-4,4'-diphenyl-ether bis-dimethylmaleimide and N,N'-4,4'-diphenylsulphone-bis-dimethylmaleimide.

It is, however, also possible to employ, for the process according to the invention, new bis-imides and tris-imides which have the following formula VIII:

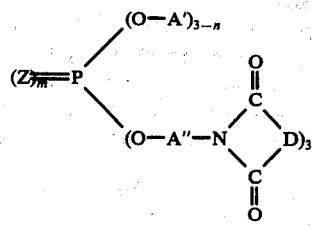
(VIII)

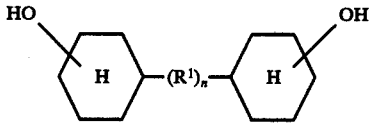
(V)

in which R¹ denotes one of the radicals —CH₂—, $$-\underset{\underset{CH_3}{|}}{\overset{\overset{CH_3}{|}}{C}}-,$$

—SO₂—, —SO—, —S— and —O— and n is 0 or 1.

Examples of such compounds are hydrogenated bisphenol A; bis-(p-hydroxycyclohexyl)-methane, bis-(p-hydroxycyclohexyl)sulphone, bis-(p-hydroxycyclohexyl)-sulphoxide, bis-(p-hydroxycyclohexyl)-sulphide, bis-(p-hydroxycyclohexyl)-ether and 4,4'-dihydroxydicyclohexyl.

In these, A and A" denote aromatic radicals which are optionally substituted or are interrupted by an oxygen atom, an alkylene group or sulphonyl group, D denotes the radical already defined above, Z denotes an oxygen atom or a sulphur atom, m denotes the number 1 or 0 and n denotes the number 2 or 3.

The new bis-imides and tris-imides of the formula VIII are obtained by cyclising dicarboxylic acid monoamide compounds of the general formula IX

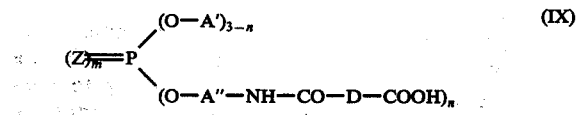
(IX)

at temperatures below 90° C in the presence of catalysts (Na and K salts) with elimination of n mols of water and subsequently isolating the compounds of the formula VII by precipitating the reaction product in water or an aqueous alcohol solution. The dicarboxylic acid monoamide compounds employed here can be manufactured according to known processes. In this context, attention should be drawn to U.S. Pat. No. 2,444,536 and GB Patent Specification No. 1,027,059.

Examples of such new maleimides suitable for the process according to the invention are: the N,N'-bis-maleimide of 4,4'-diamino-triphenyl-phosphate, the N,N'-bis-maleimide of 4,4'-diamino-triphenyl-thiophosphate, the N,N',N"-tris-maleimide of tris-(4-aminophenyl)-phosphate and the N,N',N"-tris-maleimide of tris-(4-aminophenyl)-thiophosphate.

According to the invention it is also possible to use mixtures of two or more of any of the abovementioned polyimides.

Dihydric or trihydric alcohols should be mentioned particularly as polyhydric alcohols which (optionally as a mixture of different alcohols) are suitable for use as starting materials for the process according to the invention.

Unbranched or branched aliphatic alcohols with a total of 2 to 12 C atoms, such as, for example, ethylene glycol, 1,3-propanediol, 1,4-butanediol, 1,5-pentanediol, 1,6-hexanediol, 1,8-octanediol, 1,2,6-hexanetriol, 1,1,1-trishydroxymethylpropane and glycerol are very suitable. In principle it is also possible to employ alcohols containing one or more olefinic double bonds.

Further very suitable starting materials are cycloaliphatic or cycloaliphatic-aliphatic alcohols with 1 or more cycloaliphatic nuclei which can optionally contain oxygen, sulphur or sulphur-containing radicals as linking members, the hydroxyl groups being bonded either to the aliphatic or to the cycloaliphatic radicals.

A preferred embodiment of the invention in this respect is the use of compounds which correspond to the formula V Further alcohols which are very suitable for the process according to the invention are polyglycol ethers of polyhydric alcohols or phenols, such as, for example, the diglycol ethers of the abovementioned compounds of the formula (V), especially bisphenol A diglycol ether.

Polyhydric alcohols of the formula

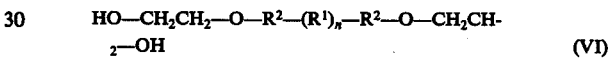
(VI)

in which R² denotes a phenylene radical or a cyclohexylene radical, are also very suitable for the process according to the invention.

Polymethylol compounds, such as, for example, cyclohexanedimethylol, should be mentioned as further suitable cycloaliphatic-aliphatic alcohols. The simplest of the purely cycloaliphatic alcohols which can be employed as a starting material is 1,4-cyclohexanediol.

All polyalcohols listed here, which are suitable as starting materials for the process according to the invention, have long been known to those skilled in the art and it is therefore superfluous to deal here with how they may be obtained.

According to the invention, aromatic or araliphatic di- or tri-primary amines with 2 to 40 C atoms in the molecule are employed preferentially. Diamines of the formula

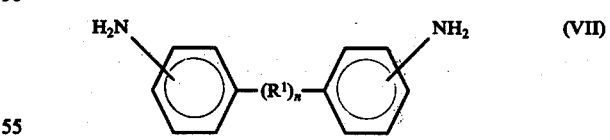
(VII)

in which R¹ and n have the abovementioned meaning, are particularly suitable.

In principle it is also possible to employ all the polyamines which have already been listed in French Pat. No. 1,555,564. In detail, the following polyamines suitable for the process according to the invention should be mentioned: 1,2,4-triaminobenzene, 1,3,5-triaminobenzene, 2,4,6-triaminotoluene, 2,4,6-triamino-1,3,5-trimethylbenzene, 1,3,7-triaminonaphthalene, 2,4,4'-triaminodiphenyl, 3,4,6-triaminopyridine, 2,4,4'-triaminophenyl-ether, 2,4,4'-triaminodiphenylmethane, 2,4,4'-triaminodiphenylsulphone, 2,4,4'-triaminobenzophenone, 2,4,4'-triamino-3-methyl-diphenylmethane, N,N,N-tri(4-aminophenyl)-amine, tri-(4-aminophenyl)-methane, tri-(4-aminophenyl)phosphate, tri-(4-aminophenyl)-phosphite, tri-(4-aminophenyl)thiophosphate, 3,5,4'-triaminobenzanilide, melamine, 3,5,3',5'-tetraaminobenzophenone, 1,2,4,5-tetraaminobenzene, 2,3,6,7-tetraaminonaphthalene, 3,3'-diaminobenzidine, 3,3',4,4'-tetraaminophenyl-ether, 3,3',4,4'-tetraaminodiphenylmethane, 3,3',4,4'-tetraaminodiphenylsulphone, 3,5-bis-(3,4'-diaminophenyl)pyridine, 4,4'-diaminodicyclohexylmethane, 1,4-diamino-cyclohexane, m-phenylenediamine, p-phenylenediamine, 4,4'-diaminodiphenyl-methane, bis-(4-aminophenyl)-2,2-propane, 4,4'-diaminodiphenyl-ether, 4,4'-diaminodiphenylsulphone, 1,5-diaminonaphthalene, m-xylylenediamine, p-xylylenediamine, ethylenediamine, hexamethylenediamine, bis-(γ-aminopropyl)-5,5-dimethyl-hydantoin and 4,4'-diaminotriphenyl-phosphate.

The abovementioned amines which are suitable for the process according to the invention, and the processes for their manufacture, are known so that it is superfluous to deal with them in more detail.

For completeness it should be mentioned that polyamines which are obtained by reaction of primary aromatic amines with aldehydes or ketones are also suitable for use as starting materials. In this respect, attention should be drawn to French Patent Specifications Nos. 1,430,977 and 1,481,932.

Mixtures of several polyamines can also be employed according to the invention.

The reaction according to the invention is preferably carried out in the melt or partly in the melt and partly in the solid phase. It can however also be carried out in solution.

Where the process is carried out in the melt, temperatures of 150° to 250° C are particularly suitable. In solution, on the other hand, lower temperatures of, for example, 50° to 150° C can also be employed.

The following substances should be mentioned as examples of suitable solvents: aromatics, such as xylene and toluene; halogenohydrocarbons, such as trichloroethylene, tetrachloroethane, tetrachloroethylene and chlorobenzene; ethers, such as dioxane, tetrahydrofurane and dibutyl ether; dimethylformamide, tetramethylurea, dimethylsulphoxide and N-methylpyrrolidone.

In some cases, particularly when using mixtures of substances of relatively low reactivity, or when carrying out the polyaddition in solution at lower temperatures, it is also advisable to accelerate the reaction by basic catalysts in case (F). The catalysts to be used are for practical purposes the same as have already been listed. They should be present in the reaction mixture in a concentration of 0.1 to 15% by weight, preferably 0.3 to 8% by weight, the % by weight data relating to the total amount of the reacting starting components.

The products produced by the reactants which contain secondary or tertiary amino groups can also act as catalysts in the course of the reaction.

In general, the process (F) according to the invention is carried out starting from reaction mixtures which in addition to the polyimides simultaneously contain polyhydric alcohols and primary polyamines.

However, an alternative possible procedure is first to allow the particular polyimide to react wholly or partly with the particular alcohol in the presence of a catalyst and then to allow the remaining reaction with the primary polyamine and, if relevant, with the remaining alcohol to take place.

The converse procedure is also possible. First, the particular polyimide can be reacted wholly or partly with the particular primary polyamine. Thereafter, the reaction with the particular polyhydric alcohol and, if appropriate, with the remaining primary polyamine is carried out.

In the two procedures last described, a prepolymer is, for practical purposes, prepared first. However, it is also possible to prepare a prepolymer as follows, and then proceed further: after mixing and, if appropriate, after subsequent grinding, of all the starting products, the powder is first heated for a limited period, preferably to 140° – 170° C. A partially soluble product which is still thermally mouldable results. This prepolymer may at times have to be re-ground to give a workable powder, before it is finally cured in the final processing. The prepolymerisation can also be effected by heating a solution or suspension of the starting materials. The prepolymer process last described is also applicable to the preferred embodiment (E).

The manufacture, according to the invention, of the polyaddition products containing imide groups is as a rule carried out with simultaneous shaping to give mouldings, sheet-like structures, laminates, adhesive bonds or foamed plastics. The additives customary in the technology of thermosetting plastics, such as fillers, plasticisers, pigments, dyestuffs, mould release agents and flameproofing substances can be added to the curable compositions. Examples of fillers which can be used are glass fibers, mica, quartz powder, kaolin, colloidal silicon dioxide or metal powders whilst examples of mould release agents which can be used are various waxes, zinc stearate, calcium stearate and the like.

The products which can be manufactured in accordance with the process of the invention can very simply be moulded by the casting process, using a casting mould.

However, they can also be moulded by hot pressing, using a press. In most cases it suffices to heat the materials only briefly to temperatures of 170° to 250° C under a pressure of 1 to 200 kp/cm² and to complete the curing of the resulting moulding outside the press.

The process according to the invention can also be carried out by first producing a prepolymer, suspending or dissolving this in a suitable solvent, then impregnating porous sheet-like structures, such as woven fabrics, fiber mats or fiber fleeces, especially glass fiber mats or glass fiber fabrics, with these solutions or suspensions, removing the solvent by a drying process and finally heating the substrates thus obtained in a press, preferably to 170° – 250° C under a pressure of 5 – 200 kp/cm² pressure. It is also possible only to precure the laminates in the press and to post-cure the products thus obtained in an oven until optimum use properties are achieved.

The process according to the invention, and the polyaddition products which can be manufactured thereby, are above all applicable in the fields of surface protection, the electrical industry, laminating processes, the manufacture of foamed plastics, and the building industry.

A further subject of the invention are storage-stable, hot-curable mixtures which are characterised in that they contain a) polyimides which contain, per molecule, at least two radicals of the general formula

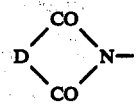

in which D denotes a divalent radical containing a carbon-carbon double bond, b) polyhydric alcohols and c) the appropriate basic compounds.

These curable mixtures are preferably mixed powders. These are obtained most advantageously by conjointly grinding, or post-grinding, the solid individual components using high intensity grinding equipment (such as, for example, ball mills). From the powder mixture, which in many cases can be employed as such, it is, however, also possible to produce in a known manner, by tabletting, by build-up granulation or by similar processes, a material containing larger particles which is, for example, particularly suitable for the hot pressing process.

If the hot-curable mixtures according to the invention are to be used as casting resins, they must not contain polyalcohols which are evolved during the requisite degassing of the mixture in the melt under reduced pressure (for example at 2 to 20 mm Hg). Thus, for example, 1,4-butanediol cannot be employed in conjunction with N,N'-4,4'-diphenylmethane-bis-maleimide for casting resin mixtures. As is known, this maleimide melts at about 150° C and the boiling point of 1,4-butanediol at 10 mm Hg is about 120° C, that is to say the latter substance would distil off during degassing of the melt.

Accordingly, a preferred embodiment of the hot-curable mixtures according to the invention are mixtures which contain polyalcohols of which the boiling points at the pressure which is generally used to degas the mixture in the melt (2 – 20 mm Hg) are above the temperature of this melt.

The above restriction on the mixtures according to the invention when they are processed by casting however does not apply to the processing of the mixtures in solution. In the latter case, for example, a combination of N,N'-4,4'-diphenylmethane-bis-maleimide with 1,4-butanediol is entirely possible.

Manufacture of starting materials for the process according to the invention

I. Manufacture of a tris-imide of the formula VIII a. 294 g (3.0 mols) of maleic anhydride, dissolved in 800 ml of dioxane, are initially introduced into a reaction vessel equipped with a stirrer and thermometer. A solution of 371 g (1 mol) of tris-(4-aminophenyl)-phosphate, dissolved in 2.5 liters of dioxane, is added dropwise to the above solution at 10°–20° C over the course of 4 – 5 hours. After completion of the addition, the mixture is stirred for a further 1½ hours and the reaction product is then filtered off, washed with chloroform and dried. 669 g of a yellowish substance of melting point 127°–130° C are obtained. According to the analytical data, this substance has the following structure:

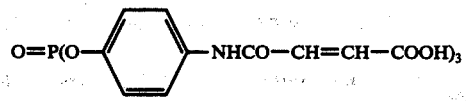

b. 85 g of sodium acetate and 1.1 liters of acetic anhydride are initially introduced into a reaction vessel equipped with a stirrer and thermometer and are warmed to 60° C by means of an oil bath. 954 g of the tris-maleamic acid manufactured according to a) are added in portions to this solution over the course of 30 minutes in such a way that the reaction temperature does not exceed 90° C. After completion of the addition, the mixture is allowed to cool to room temperature and there-after a mixture of 2 liters of isopropanol and 0.7 liter of water is added dropwise to the reaction product which has partially crystallised out. The substance which has precipitated is filtered off, washed with isopropanol and water until free from acid and dried. 532 g of a substance of melting point 173.5°–177° C are obtained; according to analytical data, this substance is the tris-maleimide of tris-(4-aminophenyl)-phosphate, and has the following structural formula:

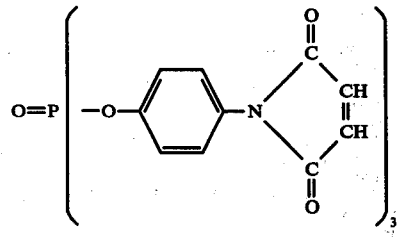

EXAMPLES OF CARRYING OUT THE INVENTION

EXAMPLE 1

179 g (0.5 mol) of N,N'-p,p'-diphenylmethane-bis-maleimide are fused and degassed at approx. 180° C oil bath temperature and 20 to 30 mm Hg. 13.5 g (0.15 mol) of 1,4-butanediol and 4.1 g (0.025 mol) of mercaptobenzothiazole as the catalyst are degassed under normal pressure at 30° to 40° C. The latter two substances are then mixed with the melt under normal pressure. The reaction mixture thus produced is immediately poured into a mould of dimensions 150 × 150 × 4 mm and heated to 205° C for 10 hours. A solid casting results, which has a heat distortion point (according to ISO/R 75) of > 300° C.

EXAMPLES 2 to 7

In the examples which follow, the casting technique is again used, as in Example 1, except that in part other reactants and catalysts, or no catalysts, are employed and that the ratios of the components are in part changed. Table 1 gives a survey of the reactants and the amounts of these which are used. The degassing of the starting materials and, where relevant, of the catalysts, is carried out conjointly or individually in the various examples. In each case, the degassing should appropriately be carried out in such a way that more readily volatile components do not evaporate. The heat distortion values are summarised in Table 2.

EXAMPLES 8 AND 9 (comparison examples)

In these examples, the technical teaching of French Patent No. 1,555,564 is followed (again using the casting technique). The ratios used are again summarised in Table 1, and the test results in Table 2. The reaction mixture was cured for 10 hours at 205° C.

Discussion of Examples 1 to 9 and of the experimental results

It can be seen from Tables 1 and 2 that the polyadducts manufactured according to the process of the invention (Examples 1 to 7) in all cases have a higher heat distortion point, and in most cases a substantially higher heat distortion point, than the polyadducts which have been manufactured according to French Patent No. 1,555,564 (Examples 8 and 9).

Table 1

| | Polyimide employed | | | Polyhydric alcohol employed | | | Catalyst employed | | |
|---|---|---|---|---|---|---|---|---|---|
| | | Amount | | | Amount | | | Amount | |
| Example | Type | g | mol | Type | g | mol | Type | g | % by weight |
| 1 | N,N'-p,p'-Diphenyl-methane-bis-maleimide | 179 | 0.5 | 1,4-Butanediol | 13.5 | 0.15 | Mercapto-benzothiazole | 4.1 | 2.1 |
| 2 | N,N'-p,p'-Diphenyl-methane-bis-maleimide | 179 | 0.5 | 1,4-Butanediol | 13.5 | 0.15 | — | — | — |
| 3 | N,N'-p,p'-Diphenyl-methane-bis-maleimide | 179 | 0.5 | 1,4-Butanediol | 13.5 | 0.15 | Benzimidazole | 2.95 | 1.5 |
| 4 | N,N'-p,p'-Diphenyl-methane-bis-maleimide | 179 | 0.5 | 1,2,6-Hexanetriol | 22.1 | 0.165 | — | — | — |
| 5 | N,N'-p,p'-Diphenyl-methane-bis-maleimide | 179 | 0.5 | 1,4-Cyclohexanediol | 29.0 | 0.25 | Benzimidazole | 5.9 | 2.8 |
| 6 | N,N'-p,p'-Diphenyl-methane-bis-maleimide | 179 | 0.5 | Hydrogenated bis-phenol A | 60.0 | 0.25 | Benzimidazole | 5.9 | 2.48 |
| 7 | Tris-phenylmaleimido-phosphate | 152.8 | 0.25 | 1,4-Butanediol | 13.5 | 0.15 | Benzimidazole | 5.9 | 3.54 |

| | | | Polyamine employed | | | | | |
|---|---|---|---|---|---|---|---|---|
| | | | | Amount | | | | |
| | | | Type | g | mol | | | |
| 8 | N,N'-p,p'-Diphenyl-methane-bis-maleimide | 1 | 4,4'-Diaminodiphenylmethane | | 0.4 | No additional catalyst | | |
| 9 | N,N'-p,p'-Diphenyl-methane-bis-maleimide | 1 | 4,4'-Diaminodiphenylmethane | | 1.0 | No additional catalyst | | |

Table 2

| Example | Heat distortion point according to ISO/R 75 °C |
|---|---|
| 1 | >300 |
| 2 | >300 |
| 3 | >300 |
| 4 | >300 |
| 5 | 275 |
| 6 | 252 |
| 7 | 223 |
| 8 | 214 |
| 9 | 196 |

EXAMPLES 10 TO 24

In these examples, the technique of Example 1 is used except that other reactants and, in part, other curing parameters are employed.

Table 3 lists the starting products and their amounts in the individual examples, and Table 4 lists the test results.

In Examples 10 and 11 curing was carried out at 245° C and in all other examples at 205° C. In all cases, the curing time was 10 hours.

Table 3

| | Polyimide employed | | | Polyhydric alcohol employed | | | Catalyst employed | | |
|---|---|---|---|---|---|---|---|---|---|
| | | Amount | | | Amount | | | Amount | |
| Example | Type | g | mol | Type | g | mol | Type | g | % by weight |
| 10 | N,N'-p-p'-Diphenyl-methane-bis-maleimide | 179 | 0.5 | Cyclohexanedimethylol | 21.6 | 0.15 | Benzimidazole | 2.95 | 1.47 |
| 11 | | 179 | 0.5 | 1,8-Octanediol | 29.9 | 0.15 | " | 2.95 | 1.40 |
| 12 | N,N'-4,4'-Diphenyl-ether-bis-maleimide | 72 | 0.2 | 1,4-Cyclohexanediol | 6.96 | 0.06 | — | — | — |
| 13 | N,N'-4,4'-Diphenyl-thioether-bis-maleimide | 75.2 | 0.2 | 1,4-Cyclohexanediol | 6.96 | 0.06 | Benzimidazole | 1.18 | 1.43 |
| 14 | N,N'-p,p'-Diphenyl-methane-bis-maleimide | 89.5 | 0.25 | 3,6-Dimethyl-3,6-octanediol | 13.07 | 0.075 | — | — | — |
| 15 | N,N'-p,p'-Diphenyl-methane-bis-maleimide | 89.5 | 0.25 | 2-Ethyl-2-methyl-1,3-propanediol | 8.25 | 0.075 | Benzimidazole | 1.47 | 1.50 |
| 16 | N,N'-p,p'-Diphenyl-methane-bis-maleimide | 89.5 | 0.25 | 2-Ethyl-2-butyl-1,3-propanediol- | 12.0 | 0.075 | " | 1.47 | 1.44 |
| 17 | N,N'-p,p'-Diphenyl-methane-bis-maleimide | 89.5 | 0.25 | Hydrogenated bisphenol A | 18.0 | 0.075 | " | 1.47 | 1.36 |

Table 3-continued

| Example | Polyimide employed Type | Amount g | mol | Polyhydric alcohol employed Type | Amount g | mol | Catalyst employed Type | Amount g | % by weight |
|---|---|---|---|---|---|---|---|---|---|
| 18 | N,N'-p,p'-Diphenyl-methane-bis-maleimide | 89.5 | 0.25 | Tetraethylene glycol | 14.55 | 0.075 | Benzimidazole | 1.47 | 1.41 |
| 19 | N,N'-p,p'-Diphenyl-methane-bis-maleimide | 268.5 | 0.75 | Diomethanedi-glycol ether | 73.9 | 0.225 | " | 4.42 | 1.29 |
| 20 | N,N'-p,p'-Diphenyl-methane-bis-maleimide | 89.5 | 0.25 | Cyclohexane-dimethylol | 10.8 | 0.075 | N-Tetramethyl-p,p'-diamino-diphenylmethane | 5.00 | 4.76 |
| 21 | N,N'-p,p'-Diphenyl-methane-bis-maleimide | 89.5 | 0.25 | Cyclohexane-dimethylol | 10.8 | 0.075 | N-Tetramethyl-p,p'-diamino-diphenylmethane | 10.00 | 9.09 |
| 22 | N,N'-p,p'-Diphenyl-methane-bis-maleimide | 89.5 | 0.25 | Cyclohexane-dimethylol | 10.8 | 0.075 | N-Tetramethyl-p,p'-diamino-diphenylmethane | 15.00 | 13.04 |
| 23 | N,N'-p,p'-Diphenyl-methane-bis-maleimide | 89.5 | 0.25 | Cyclohexane-dimethylol | 10.8 | 0.075 | Sodium methylate | 1.35 | |
| 24 | N,N'-p,p'-Diphenyl-methane-bis-maleimide | 89.5 | 0.25 | Cyclohexane-dimethylol | 10.8 | 0.075 | Tetramethyl-ammonium bromide | 5.25 | |

Table 4

| Example | Flexural strength according to VSM 77,103* kg/mm² | Impact strength according to VSM 77,105* cmkg/cm² | Heat distortion point according to ISO/R 75** ° C |
|---|---|---|---|
| 10 | 10.0 | 9.0 | >300 |
| 11 | 8.9 | 7.6 | >300 |
| 12 | 7.3 | 3.7 | 241 |
| 13 | 6.4 | 2.9 | 291 |
| 14 | 3.9 | 1.3 | 252 |
| 15 | 8.0 | 7.7 | >300 |
| 16 | 9.3 | 8.0 | >300 |
| 17 | 8.1 | 8.5 | 292 |
| 18 | 8.7 | 11.5 | 300 |
| 19 | 10.1 | 7.8 | — |
| 20 | 7.4 | 4.3 | >300 |
| 21 | 8.6 | 4.9 | 279 |
| 22 | 11.05 | 5.5 | 255 |
| 23 | 4.1 | 1.8 | >300 |
| 24 | 3.9 | 1.4 | 290 |

*VSM = Standards of the Vereins Schweizerischer Maschinenindustrieller
**ISO/R Standards of the International Standard Organisation/Recommendation

EXAMPLES OF CARRYING OUT THE INVENTION IN ACCORDANCE WITH THE PREFERRED EMBODIMENT (F)

EXAMPLE 25

179 g (0.5 mol) of N,N'-p,p'-diphenylmethane-bis-maleimide and 9.9 g (0.05 mol) of 4,4'-diaminodiphenylmethane are fused together at approx. 180° C oil bath temperature. After degassing at 20-30 mm Hg, 13.5 g (0.15 mol) of 1,4-butanediol are admixed under normal pressure. Immediately thereafter, the resulting clear melt is poured into moulds of size 150 × 150 × 4 mm and cured for 10 hours at 205° C. A casting which has a heat distortion point (according to ISO/R 75) of > 300° C is produced.

EXAMPLES 26 TO 33

In the examples which follow, the procedure adopted is analogous to Example 25 except that, in part, other reactants are employed and that, in part, the ratios of the components are modified. Table 5 gives a survey of the reactants and the amounts thereof which are employed. The degassing of the starting materials is carried out conjointly or individually in the various examples. In each case, the degassing should suitably be carried out in such a way that more readily volatile components do not evaporate. The properties of the end products are listed in Table 6.

DISCUSSION OF THE EXAMPLES AND EXPERIMENTAL RESULTS (25 – 33 and 8 and 9)

It can be seen from Tables 5 and 6 that the polyadducts manufactured in accordance with the process of the invention (preferred embodiment F) (Examples 25 to 33) in all cases show a higher heat distortion point than the polyadducts which have been manufactured according to French Pat. No. 1,555,564 (Examples 8 and 9). In most cases the impact strength is as high, or higher, than in the case of the products manfactured in accordance with known processes. The flexural strength is sufficiently high if the optimum formulation is used.

Table 5

| Example | Polyimide employed Type | Amount g | mol | Polyhydric alcohol employed Type | Amount g | mol | Polyamine employed Type | Amount g | mol |
|---|---|---|---|---|---|---|---|---|---|
| 25 | N,N'-p,p'-Diphenyl-methane-bis-maleimide | 179 | 0.5 | 1,4-Butanediol | 13.5 | 0.15 | 4,4'-Diaminodiphenylmethane | 9.9 | 0.05 |

Table 5-continued

| Example | Polyimide employed Type | Amount g | Amount mol | Polyhydric alcohol employed Type | Amount g | Amount mol | Polyamine employed Type | Amount g | Amount mol |
|---|---|---|---|---|---|---|---|---|---|
| 26 | " | 179 | 0.5 | " | 9.0 | 0.10 | " | 39.6 | 0.2 |
| 27 | " | 179 | 0.5 | Ethylene glycol | 6.2 | 0.10 | " | 39.6 | 0.2 |
| 28 | " | 179 | 0.5 | 1,8-Octanediol | 14.6 | 0.10 | " | 39.6 | 0.2 |
| 29 | " | 179 | 0.5 | 1,4-Cyclohexane-diol | 34.8 | 0.30 | " | 39.6 | 0.2 |
| 30 | " | 179 | 0.5 | Cyclohexane-1,4-dimethanol | 28.8 | 0.20 | " | 39.6 | 0.2 |
| 31 | " | 179 | 0.5 | 1,4-Butanediol | 13.5 | 0.15 | " | 39.6 | 0.2 |
| 32 | " | 179 | 0.5 | 1,4-Butanediol | 4.5 | 0.05 | " | 39.6 | 0.2 |
| 33 | " | 179 | 0.5 | 1,4-Butanediol | 27.0 | 0.3 | " | 39.6 | 0.2 |
| 8 | " | | 1.0 | — | — | — | " | | 0.4 |
| 9 | " | | 1.0 | — | — | — | " | | 1.1 |

Table 6

| Example | Flexural strength according to VSM 77,103* kg/mm² | Impact strength according to VSM 77,105* cmkg/cm² | Heat distortion point according to ISO/R 75** °C |
|---|---|---|---|
| 25 | 7.5 | 3.8 | >300 |
| 26 | — | 15.4 | 250 |
| 27 | 13.0 | 15.6 | 235 |
| 28 | 14.9 | 13.4 | 236 |
| 29 | — | 15.2 | 226 |
| 30 | — | 11.1 | 256 |
| 31 | 16.3 | 17.9 | 234 |
| 32 | — | 11.9 | 245 |
| 33 | — | 15.6 | 238 |
| 8 | 13.3 | 14.0 | 214 |
| 9 | 19.2 | 15.9 | 196 |

*VSM = Standards of the Vereins Schweizerischer Maschinenindustrieller
**ISO/R = Standards of the International Standard Organisation/Recommendation

EXAMPLES 34 TO 47

In these examples, the technique of Examples 25 to 33 is used. Table 7 lists the starting materials and the amounts thereof and Table 8 lists the test results. In Examples 34 and 35, curing was carried out at 245° C, whilst in all other examples it was carried out at 205° C. In all cases the curing time was again 10 hours.

Table 7

| Example | Polyimide employed Type | Amount g | Amount mol | Polyhydric alcohol employed Type | Amount g | Amount mol | Polyamine employed Type | Amount g | Amount mol |
|---|---|---|---|---|---|---|---|---|---|
| 34 | N,N'-p,p'-Diphenyl-methane-bis-maleimide | 179 | 0.5 | Cyclohexanedimethylol | 21.6 | 0.15 | 4,4'-Diaminodiphenylmethane | 19.8 | 0.1 |
| 35 | " | 179 | 0.5 | 1,8-Octanediol | 21.9 | 0.15 | " | 19.8 | 0.1 |
| 36 | The tris-imide of the formula VIII according to preparation Example 1 | 59.5 | 0.1 | " | 7.3 | 0.05 | " | 5.9 | 0.03 |
| 37 | N,N'-4,4'-Diphenyl-ether-bis-maleimide | 72 | 0.2 | Cyclohexanediol | 6.96 | 0.06 | " | 7.92 | 0.04 |
| 38 | N,N'-4,4'-Diphenyl-thioether-bis-maleimide | 75.3 | 0.2 | " | 6.96 | 0.06 | " | 7.92 | 0.04 |
| 39 | N,N'-p,p'-Diphenyl-methane-bis-maleimide | 89.5 | 0.25 | Cyclohexanedimethylol | 7.2 | 0.05 | m-Phenylenediamine | 5.4 | 0.05 |
| 40 | " | 89.5 | 0.25 | " | 7.2 | 0.05 | 1,12-Diaminodecane | 10.0 | 0.05 |
| 41 | " | 89.5 | 0.25 | " | 7.2 | 0.05 | 4,4'-Diaminodiphenyl-ether | 10.0 | 0.05 |
| 42 | N,N'-p,p'-Diphenyl-methane-bis-maleimide | 89.5 | 0.25 | 3,6-dimethyl-3,6-octanediol | 8.71 | 0.05 | 4,4'-Diaminodiphenylmethane | 9.9 | 0.05 |
| 43 | " | 89.5 | 0.25 | 2-Ethyl-2-methyl-1,3-propanediol | 8.85 | 0.075 | " | 9.9 | 0.05 |
| 44 | " | 89.5 | 0.25 | 2-Ethyl-2-butyl-1,3-propanediol | 12.0 | 0.075 | " | 9.9 | 0.05 |
| 45 | " | 89.5 | 0.25 | Hydrogenated bisphenol A | 18.0 | 0.075 | " | 9.9 | 0.05 |
| 46 | " | 89.5 | 0.25 | Tetraethyleneglycol | 14.55 | 0.075 | " | 9.9 | 0.05 |
| 47 | " | 268.5 | 0.75 | Diomethane diglycol ether | 41.0 | 0.125 | " | 29.7 | 0.15 |

Table 8

| Example | Flexural strength according to VSM 77,103* kg/mm² | Impact strength according to VSM 77,105* cmkg/cm² | Heat distortion point according to ISO/R 75** °C |
|---|---|---|---|
| 34 | 12.2 | 10.8 | >300 |

Table 8-continued

| Example | Flexural strength according to VSM 77,103* kg/mm² | Impact strength according to VSM 77,105* cmkg/cm² | Heat distortion point according to ISO/R 75** °C |
| --- | --- | --- | --- |
| 35 | 9.9 | 10.2 | >300 |
| 36 | 14.5 | 9.8 | 222 |
| 37 | 12.1 | 5.9 | 300 |
| 38 | 3.6 | 1.8 | 231 |
| 39 | 6.7 | 4.3 | 266 |
| 40 | 6.9 | 1.2 | >300 |
| 41 | 10.5 | 6.9 | 248 |
| 42 | 9.7 | 6.3 | 292 |
| 43 | 8.0 | 9.6 | 272 |
| 44 | 10.1 | 9.3 | 285 |
| 45 | 11.9 | 8.8 | 242 |
| 46 | 11.2 | 11.0 | >300 |
| 47 | 11.7 | 11.7 | — |

*VSM = Standards of the Vereins Schweizerischer Maschinenindustrieller
**ISO/R = Standards of the International Standard Organisation/Recommendation

What we claim is:

1. Process for the manufacture of polyaddition products containing imide groups, said process comprising reacting polyimides which contain, per molecule, at least two radicals of the general formula

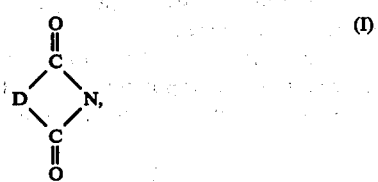

in which D denotes a divalent radical containing a carbon-carbon double bond, with polyhydric alcohols in the presence of basic compounds selected from the group consisting of primary polyamines, basic catalysts, and mixtures of primary polyamines and basic catalysts at temperatures between 50° and 280° C.

2. Process according to claim 1, wherein the reaction is allowed to take place at temperatures of 100° to 250° C.

3. Process according to claim 1, wherein polyimides with radicals of the formula (I), in which D represents a divalent radical of the formula

wherein R denotes hydrogen or methyl, are employed.

4. Process according to claim 1, wherein polyimides which contain two or three radicals of the formula (I) per molecule are employed.

5. Process according to claim 1, wherein the polyimide employed is a compound of the general formula

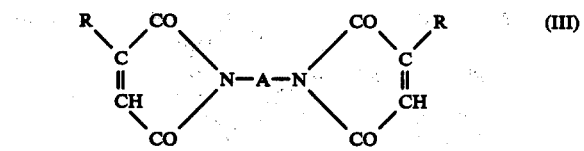

in which A denotes a divalent organic radical with 2 to 30 C atoms.

6. Process according to claim 5, wherein the polyimide employed is a compound of the formula (III) in which A denotes a radical of the formula

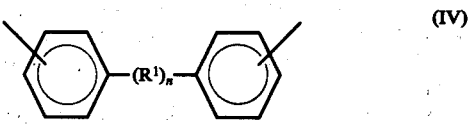

wherein $R^1$ is one of the radicals —CH$_2$—,

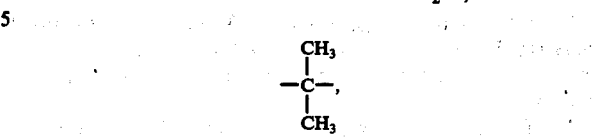

—SO$_2$—, —SO—, —S— and —O— and $n$ is 0 or 1.

7. Process according to claim 6, wherein N,N'-4,4'-diphenylmethane-bis-maleimide is employed as the polyimide.

8. Process according to claim 1, wherein a dihydric or trihydric alcohol is employed as the polyhydric alcohol.

9. Process according to claim 1, wherein an unbranched or branched aliphatic alcohol with a total of 2 to 12 C atoms is employed as the polyhydric alcohol.

10. Process according to claim 1, wherein the polyhydric alcohol employed is a cycloaliphatic or cycloaliphatic-aliphatic alcohol with 1 or more cycloaliphatic nuclei, which can optionally contain oxygen, sulphur or sulphur-containing radicals as linking members, and wherein the hydroxyl groups can be bonded either to the aliphatic or to the cycloaliphatic radicals.

11. Process according to claim 10, wherein the polyhydric alcohol employed is a compound of the formula

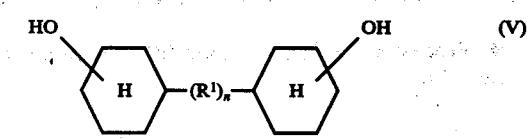

in which $R^1$ is one of the radicals —CH$_2$—,

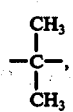

—SO$_2$—, —SO—, —S— and —O— and $n$ is 0 or 1.

12. Process according to claim 1, wherein the polyhydric alcohol employed is a polyglycol ether of a polyhydric alcohol or polyhydric phenol.

13. Process according to claim 12, wherein the polyhydric alcohol employed is a compound of the formula

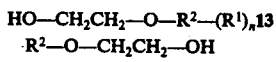

(VI)

in which $R^2$ denotes a phenylene or a cyclohexylene radical, $R^1$ is one of the radicals —CH$_2$—,

—SO$_2$—, —SO—, —S— and —O— and $n$ is 0 or 1.

14. Process according to claim 1, wherein a catalyst is employed as the basic compound.

15. Process according to claim 14, wherein the basic catalysts are employed in a concentration of 0.01 to 15% by weight, relative to the total amount of the reactants.

16. Process according to claim 14, wherein the catalysts are employed in a concentration of 0.05 to 10% by weight.

17. Process according to claim 14, wherein the catalysts employed are tertiary, secondary or mixed tertiary-secondary amines or quaternary ammonium compounds.

18. Process according to claim 14, wherein alkali metal compounds are employed as the catalysts.

19. Process according to claim 14, wherein the particular polyimide is reacted with the particular polyhydric alcohol in such a ratio as to provide 0.1 to 1 equivalent of polyhydric alcohol per 1 equivalent of polyimide.

20. Polyaddition products manufactured according to the process of claim 14.

21. Process according to claim 1, wherein the basic compounds employed are primary polyamines in such a ratio as to provide, per 1 equivalent of polyimide, such an amount of polyhydric alcohol and primary polyamine that the sum of the equivalents of said alcohol and said polyamine is 0.2 to 1.5 equivalents and the equivalent ratio of said alcohol to said polyamine is 1:4 to 4:1.

22. Process according to claim 21, wherein the reaction is allowed to take place using a ratio of the amounts to correspond to a ratio of equivalents of polyhydric alcohol to equivalents of polyamine of 1:2 to 4:1.

23. Process according to claim 21, wherein the primary polyamine employed is an aromatic or an araliphatic, di-primary or tri-primary, amine with 2 to 40 C atoms.

24. Process according to claim 21, wherein a compound of the formula

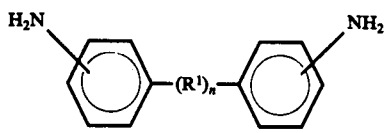

(VII)

in which $R^1$ is one of the radicals —CH$_2$—,

—SO$_2$—, —SO—, —S— and —O— and $n$ is 0 or 1 is employed as the primary polyamine.

25. Process according to claim 24, wherein that 4,4'-diaminodiphenylmethane is employed.

26. Process according to claim 21, wherein that the reaction is allowed to take place in the presence of basic catalysts which differ from the products produced during the reaction, in a concentration of 0.1 to 15% by weight relative to the total amount of the reactants.

27. Process according to claim 21, wherein that tertiary, secondary or mixed tertiary-secondary amines or quaternary ammonium compounds are employed as catalysts.

28. Process according to claim 21, wherein that alkali metal compounds are employed as catalysts.

29. Process according to claim 26, wherein the catalysts are employed in a concentration of 0.3 to 8% by weight.

30. Process according to claim 1, wherein it starts from a reaction mixture which in addition to the polyimides simultaneously contains polyhydric alcohols and primary polyamines.

31. Storage-stable, hot-curable mixtures, said mixtures comprising a) polyimides which contain, per molecule, at least two radicals of the general formula

(I)

in which D denotes a divalent radical containing a carbon-carbon double bond, b) polyhydric phenols and c) basic compounds selected from the group consisting of primary polyamines, basic catalysts, and mixtures of primary polyamines and basic catalysts.

32. Mixtures according to claim 31, which contains polyimides with radicals of the formula (I) in which D represents a divalent radical of the formula

(II)

wherein R denotes hydrogen or methyl.

33. Mixtures according to claim 31, which contains polyimides which possess two or three radicals of the formula (I) per molecule.

34. Mixtures according to claim 32, which contains as the polyimide, a compound of the general formula

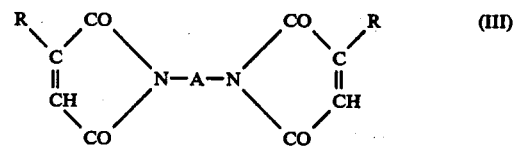

(III)

in which A denotes a divalent organic radical with 2 to 30 C atoms.

35. Mixtures according to claim 34, which contain as the polyimide, a compound of the formula (III), in which A denotes a radical of the formula

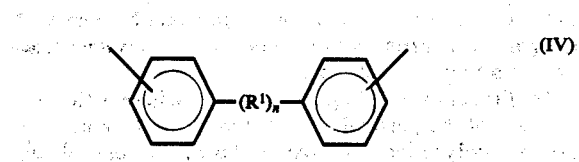

wherein R¹ represents one of the radicals —CH₂,

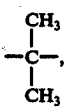

—SO₂—, —SO—, —S— and —O— and n is 0 or 1.

36. Mixtures according to claim 35, which contain N,N'-4,4'-diphenylmethane-bis-maleimide as the polyimide.

37. Mixtures according to claim 31, which contains a dihydric or trihydric alcohol as the polyhydric alcohol.

38. Mixtures according to claim 31, which contains an unbranched or branched aliphatic alcohol with a total of 2 to 12 C atoms as the polyhydric alcohol.

39. Mixtures according to claim 31, which contain, as the polyhydric alcohol, a cycloaliphatic or cycloaliphatic-aliphatic alcohol with 1 or more cycloaliphatic nuclei or a cycloaliphatic or cycloaliphatic-aliphatic alcohol with 1 or more cycloaliphatic nucleii which contains oxygen, sulphur or sulphur-containing radicals as linking members, and wherein the hydroxyl groups can be bonded either to the aliphatic or to the cycloaliphatic radicals.

40. Mixtures according to claim 39, which contains as the polyhydric alcohol, a compound of the formula

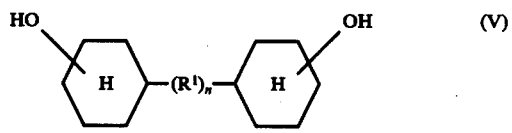

in which R¹ represents one of the radicals —CH₂—,

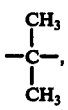

—SO₂—, —SO—, —S— or —O— and n is 0 or 1.

41. Mixtures according to claim 31, which contains as the polyhydric alcohol, a polyglycol ether of a polyhydric alcohol or polyhydric phenol.

42. Mixtures according to claim 41, which contains as the polyhydric alcohol, a compound of the formula

HO—CH₂CH₂—O—R²—(R¹)ₙ—R²—O—CH₂CH₂—OH  (VI)

in which R² denotes a phenylene radical or a cyclohexylene radical, R¹ is one of the radicals —CH₂—,

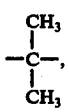

ps —SO₂—, —SO—, —S— and —O— and n is 0 and 1.

43. Mixtures according to claim 31, which contain a catalyst as the basic compound.

44. Mixtures according to claim 43, which contain the basic catalysts in a concentration of 0.01 to 15% by weight, relative to the total amount of the reactants.

45. Mixtures according to claim 43, which contain the basic catalysts in a concentration of 0.05 to 10% by weight.

46. Mixtures according to claim 43, which contain tertiary, secondary or mixed tertiary-secondary amines or quaternary ammonium compounds as catalysts.

47. Mixtures according to claim 43, which contain alkali metal compounds as catalysts.

48. Mixtures according to claim 43, which contain the particular polyimide and the particular polyhydric alcohol in such a ratio as to provide 0.1 to 1 equivalent of polyhydric alcohol per 1 equivalent of polyimide.

49. Mixture according to claim 31, said mixtures comprising primary polyamines as basic compounds wherein the reactants are present in such a ratio as to provide, per 1 equivalent of polyimide, such an amount of polyhydric alcohol and primary polyamine that the sum of the equivalents of said alcohol and said polyamine is 0.2 to 1.5 equivalents and the equivalent ratio of said alcohol to said polyamine is 1:4 to 4:1.

50. Mixtures according to claim 49, which contain an aromatic or an araliphatic, di-primary or tri-primary amine with 2 to 40 C atoms as the primary polyamine.

51. Mixtures according to claim 50, which contain a compound of the formula

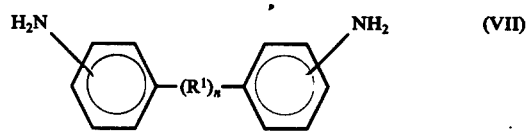

wherein R¹ is one of the radicals —CH₂—,

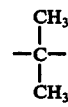

—SO₂—, —SO—, —S— —O— and n is 0 or 1, as the primary polyamine.

52. Mixtures according to claim 51, which contains 4,4'-diaminodiphenylmethane.

53. Mixtures according to claim 49, which contain basic catalysts which differ from the products formed during the reaction, in a concentration of 0.1 to 15% by weight, relative to the total amount of the reactants.

54. Mixtures according to claim 53, which contains the basic catalysts in a concentration of 0.3 to 8% by weight.

55. Mixtures according to claim 53, which contains tertiary, secondary or mixed tertiary-secondary amines or quaternary ammonium compounds as catalysts.

56. Mixtures according to claim 53, said mixtures comprising alkali metal compounds as catalysts.

57. Mixtures according to claim 49, wherein the polyhydric alcohol and the polyamine are present in the mixtures in such amounts that the equivalent ratio is 1:2 to 4:1.

58. Process for the manufacture of polyaddition products containing imide groups, said process comprising reacting polyimides which contain, per molecule, at least two radicals of the formula (I) of claim 1 with polyhydric alcohols in the presence of primary polyamines and basic catalysts as basic compounds at temperatures between 50° and 280° C.

59. Storage-stable, hot-curable mixtures, said mixtures comprising a) polyimides which contain, per molecule, at least two radicals of the formula (I) of claim 1, b) polyhydric phenols and c) primary polyamines and basic catalysts as basic compounds.

60. Process according to claim 21, wherein first the reaction of the particular polyimide with the particular polyhydric alcohol is allowed to take place completely or partially, in the presence of a catalyst, and thereafter the reaction of the reaction mixture thus obtained with the particular primary polyamine, or the terminal reaction, is allowed to take place.

61. Process according to claim 21, wherein first the reaction of the particular polyimide with the particular primary polyamine is allowed to take place, completely or partially, and thereafter the reaction of the reaction mixture, thus obtained, with the particular polyhydric alcohol, or the terminal reaction, is allowed to take place.

* * * * *